(12) United States Patent
Konwinski et al.

(10) Patent No.: US 7,404,973 B2
(45) Date of Patent: Jul. 29, 2008

(54) BOWMAN-BIRK INHIBITOR SOY PROTEIN CONCENTRATE COMPOSITION

(75) Inventors: Arthur H. Konwinski, Fort Wayne, IN (US); Charles W. Monagle, Fort Wayne, IN (US); Navpreet Singh, Fort Wayne, IN (US); Bernard F. Szuhaj, Fort Wayne, IN (US)

(73) Assignee: Solae, LLC, St. Louis, MO (US)

( * ) Notice: Subject to any disclaimer, the term of this patent is extended or adjusted under 35 U.S.C. 154(b) by 872 days.

(21) Appl. No.: 10/196,778

(22) Filed: Jul. 17, 2002

(65) Prior Publication Data

US 2003/0064121 A1 Apr. 3, 2003

Related U.S. Application Data

(60) Provisional application No. 60/306,295, filed on Jul. 18, 2001.

(51) Int. Cl.
*A61K 35/78* (2006.01)

(52) U.S. Cl. ........................................ 424/757; 514/783

(58) Field of Classification Search ............ 424/726.06; 514/783
See application file for complete search history.

(56) References Cited

U.S. PATENT DOCUMENTS

| 4,793,996 A | | 12/1988 | Kennedy et al. | |
| 5,086,166 A | * | 2/1992 | Lawhon et al. | 530/378 |
| 5,217,717 A | | 6/1993 | Kennedy et al. | |
| 5,505,946 A | * | 4/1996 | Kennedy et al. | 424/757 |
| 6,107,287 A | | 8/2000 | de Lumen et al. | |

FOREIGN PATENT DOCUMENTS

WO        WO 02/15712 A2      2/2002

OTHER PUBLICATIONS

International Search Report mailed Dec. 23, 2002.

* cited by examiner

*Primary Examiner*—Ralph Gitomer
(74) *Attorney, Agent, or Firm*—Holly M. Amjad; James L. Cordek

(57) ABSTRACT

A Bowman-Birk Inhibitor Concentrate (BBIC) that has a high protein content. The BBIC is made from conventional soybeans using ultrafiltration, without acid or alcohol extraction or acetone precipitation.

7 Claims, No Drawings

BOWMAN-BIRK INHIBITOR SOY PROTEIN CONCENTRATE COMPOSITION

RELATED APPLICATION

This application is based on and claims priority to U.S. Provisional Patent Application Ser. No. 60/306,295, filed Jul. 18, 2001, the complete disclosure of which is expressly incorporated herein by reference.

FIELD OF THE INVENTION

This invention relates to a Bowman-Birk Inhibitor Concentrate (BBIC) that has a high protein content. The BBIC is made from conventional soybeans with ultrafiltration, and without acid or alcohol extraction or acetone precipitation.

BACKGROUND OF THE INVENTION

The benefits of soy protein are well documented. Cholesterol is a major concern with consumers throughout the industrialized world. It is well known that vegetable products contain no cholesterol. For decades, nutritional studies have indicated that the inclusion of soy protein in the diet actually reduces serum cholesterol levels in humans. The higher the cholesterol, the more effective soy proteins are at lowering that level.

Soybeans have the highest protein content of all cereals and legumes. In particular, soybeans have about 40 wt. % protein, while other legumes have 20-30 wt. %, and cereals have about 8-15 wt. % protein. Soybeans also contain about 20 wt. % oil with the remaining dry matter being mostly carbohydrates (35 wt. %). On a wet basis (as is), soybeans contain about 35 wt. % protein, 17 wt. % oil, 31 wt. % carbohydrates, and 4.4 wt. % ash.

In the soybean, both storage protein and lipid bodies are contained in the usable meat of the soybean (called the cotyledon). The complex carbohydrate (or dietary fiber) is also contained in the cell walls of the cotyledon. The outer layer of cells (called the seed coat) makes up about 8 wt. % of the soybean's total weight. The raw, dehulled soybean is, depending on the variety, approximately 18 wt. % oil, 15 wt. % soluble carbohydrates, 15 wt. % insoluble carbohydrates, 14 wt. % moisture and ash, and 38 wt. % protein.

In processing, soybeans are carefully selected for color and size. The soybeans are then cleaned, conditioned (to make removal of the hull easier) and cracked, dehulled and rolled into flakes. The flakes are subjected to a solvent bath that removes the oil. The solvent is removed and the flakes are dried, creating the defatted soy flakes that are the basis of most of the soy protein products. Despite the large number of products on the market, there are only three types of soy protein: flours, isolates, and concentrates.

Soy flours are the simplest forms of soy protein, having a protein content of approximately 50 wt. %. Simply grinding and screening the defatted flakes produces soy flours. This simple processing leaves the soy flour with many of the soybean's characteristics. The lack of processing also makes soy flours highly variable in terms of quality.

Soy flours and grits are still widely produced and are used most often in baked goods, snack foods and pet foods applications where the high flavor profile does not pose a problem. Textured soy flours were an early attempt at simulating or enhancing the texture of meat products. Texturizing does not change the composition of soy flours and reduces the flavor profile only slightly. Their primary applications are inexpensive meat products or pet foods.

Soy concentrates have at least 60 wt. % protein and typically have about 70 wt. % protein. A myriad of applications has been developed for soy concentrates and texturized concentrates in processed foods, meat, poultry, fish, cereal and dairy systems.

Soy protein concentrates are made by removing soluble carbohydrate material from defatted soy meal. Aqueous alcohol extraction (60-80% ethanol) or acid leaching (isoelectric pH 4.5) are the most common means for carbohydrate removal. In both aqueous alcohol extraction and acid leaching, however, essentially all of the protein is rendered insoluble. Protein solubility may be recovered in acid leach products by neutralization.

Isolates are produced through standard chemical isolation, drawing the protein out of the defatted flake through solubilization (alkali extraction at pH 7-10) and separation followed by isoelectric precipitation. As a result, isolates are 90 wt. % protein on a moisture-free basis. Isolates can be made with a high percentage of soluble protein and a low flavor profile. They contain no dietary fiber and are sometimes high in sodium, properties that can limit their application. Their major applications have been in dairy substitution, as in infant formulas and milk replacers.

Bowman-Birk Inhibitor Concentrate (BBIC) has been shown to exhibit inhibitory activity against the malignant transformation of cells under certain conditions and its administration has been shown to affect various forms of cancer.

It has been shown that the enzyme-inhibitor described by Bowman (Proc. Soc. Expd. med, 63:547 (1946)) and Birk et al. (Bull. Res. Council Israel, Sec. A 11:48 (1962) and Biochim. Biophys Acta, 67:326 (1963)), and subsequently referred to as the Bowman-Birk Inhibitor (BBI), can prevent, or greatly reduce, radiologically or chemically induced malignant transformation of cells in culture and in experimental animals.

Yavelow et al. (Proc. Natl. Acad. Sci, USA 82:5395-5399 (1985)) reported that a crude soybean extract, if defatted with acetone, effectively blocked cell transformation in vitro. An active component of this crude extract is BBI. These observations, with epidemiological data, suggested BBI as a putative dietary anticarcinogen, particularly with respect to colon cancer.

Weed et al. (Carcinogenesis, 6:1239-1241 (1985)) discloses that an extract of soybeans containing the Bowman-Birk protease inhibitor added to the diet of dimethylhydrazine (DMH)-treated mice resulted in a significant suppression of odenomatous tumors of the colonic mucosa. DMH-induced colon cancer in mice is generally regarded as an excellent animal model for the human disease, with carcinogen treatment inducing adenocarcinomas of the colon and rectum which are similar to the tumors arising in the human colon suggesting the possibility that a dietary additive of the sort studied might confer some protection against the development of human colon cancer without undesirable side effects. BBI extract and methods for its preparation were as described by Yavelow et al. Cancer Res., 43:2454-2459 (1983); Proc. Natl. Acad. Sci., USA 82:5395-5399 (1985) and Hwang et al. Biochim. Biophys. Acta, 495:369-382 (1977).

Messadi et al. (JNCL 76:447-452 (1986)) demonstrated that a soybean extract containing the protease inhibitor BBI suppresses 7,12-dimethyl-benz[a]anthracene (DMBA)-induced carcinogenesis in the hamster cheek pouch. This oral cancer model, with the use of the hamster cheek pouch carcinogenesis system, has the same histopathology, growth pattern, and precancerous lesions as the most common form of human oral cancer, squamous cell carcinoma. It was shown in this study that hamster cheek pouch carcinogenesis can be inhibited by BBI and suggested that human oral carcinogenesis might respond to BBI in a comparable manner. The BBI preparation used in this study was a crude extract of the inhibitor prepared as described by Yavelow et al. (Proc. Nad. Acad. Sci., USA 82:5395-5399 (1985)).

Baturay et al. (Cell Biology and Toxicology, 2:21-32 (1986)) discloses that a BBI preparation, wherein a crude soybean extract is defatted with acetone, suppresses radiation and chemically induced transformation in vitro, with or without enhancement by the co-carcinogen, pyrene. Yavelow et al., 1985, supra, show that either pure BBI or the BBI extract prepared in accordance with their methods suppresses radiation induced transformation in C3H10TI12 cells. Kennedy et al, Proc. Nat'l. Acad. Sci. USA 1984, 81, 1827-39 reports that either pure BBI or the BBI extract prepared in accordance with their method reduce the levels of chromosome abnormalities in cells of patients with Bloom's syndrome (a genetic disease in which the high levels of chromosome abnormalities are thought to predispose the patients to a higher than normal cancer incidence). Still, other studies suggest that soybean-derived protease inhibitors can have suppressive effects on skin, breast and liver carcinogenesis in vivo.

Kennedy et al. in Anticarcinooenesis and Radiation Protection, edited by Cerutti et al., Plenum Pub. Co., pp. 285-295 (1987), disclosed that BBI suppresses carcinogenesis in various systems using a crude BBI extract prepared by defatting soybeans with acetone. Their results suggested that very low concentrations of BBI-type protease inhibitor preparations would be effective as chemopreventative agents for colon cancer. There was no evidence to suggest that the use of protease inhibitors as chemopreventative agents would be complicated by possible toxicity problems.

St. Clair et al. (Cancer Res., 50:580-586 (1990)) report that the addition of 0.5% or 0.1% semi-purified BBI or 0.1% or 0.01% purified BBI to the diet of DMH-treated mice resulted in a statistically significant suppression of angiosarcomas and nodular hyperplasia of the liver and colon carcinogenesis. The results of this study also indicate that BBI, included as 0.5% of the diet or less had no adverse effect upon the health of the mice but had the capacity to suppress liver and colon carcinogenesis.

Perlmann et al. (Methods in Enzymology, 19: 860-861 (1970)) describes an elaborate method for obtaining the BBI from a defatted soybean extract.

U.S. Patent No. 4,793,996 to Kennedy et al. discloses a process of treating soybeans with acetone, followed by ethanol extraction and acetone precipitation for obtaining BBI. The soybeans may be defatted prior to acetone treatment. In addition, BBI may be further purified by conventional techniques. Kennedy et al. discovered that by treating the soybeans with acetone prior to the ethanol extraction step taught by Perlmann et al., the resulting BBI was more effective in inhibiting the malignant transformation of cells.

U.S. Pat. No. 4,793,996 to Kennedy et al. teaches a process for preparing a crude soybean extract containing a BBI inhibitor of malignant cell transformation which involves defatting soybeans and extracting the inhibitor from the defatted soybeans, and, as an improvement that greatly increases the effectiveness of the BBI inhibitor, defatting the soybeans by bringing them into contact with at least an equal weight of acetone. This process thus produces a crude inhibitor extract which, due to the contact with acetone, nevertheless demonstrates greatly increased effectiveness.

U.S. Pat. No. 5,217,717 to Kennedy et al. teaches ultrafiltration of soy solubles, including a whey protein, to make a BBIC. The ultrafiltration process may be performed alone, or in combination with acetone precipitation, prior to or after the ultrafiltration.

U.S. Pat. No. 5,217,717 to Kennedy et al. also teaches performing two acetone extractions of soy solubles to produce a BBIC, without ultrafiltration. The patentees discovered that spray-drying has no effect on BBI recovery, as measured by chymotrypsin inhibition (CI), used as an indicator for the presence of BBI.

Lunasin is a major component of the Bowman-Birk protease inhibitor from soybeans. Research conducted at the University of California at Berkeley found that lunasin binds to a protein that itself binds to DNA, blocking a step that normally leads to multiplication of cancer cells. Injecting the lunasin-bound protein into cells stops cell division in both normal and cancerous cells. This discovery has lead to the successful use of lunasin in treating human breast cancer cells, and skin cancer in mice, and has spurred research directed to finding delivery systems for lunasin for cancer prevention and treatment.

The prior art has not described a high protein concentrate having high levels of BBI that is obtained from a soy protein source, without acid or alcohol extraction, or acetone precipitation. The prior art also has not described a high protein concentrate having high levels of BBI that is obtained from a fiber-removed soy protein source. The prior art also has not described a high protein concentrate that includes acetone-free BBI. In the present invention, a high protein concentrate having high levels of BBI is produced from a soy protein source, without acid or alcohol extraction, or acetone precipitation.

SUMMARY OF THE INVENTION

The present invention is directed to an acetone-free Bowman-Birk inhibitor product having: (i) greater than 65 wt. % soy protein of total dry matter and (ii) a chymotrypsin inhibitor (CI) level of at least 110 milligrams/gram. In another embodiment, the present invention is directed to a method for manufacturing a protein product which method involves: (a) providing a substantially defatted soybean material; (b) removing fiber from said material, and (c) achieving a desired CI content by ultrafiltration. The resulting product, which can be dried, is then used in a pharmaceutical composition or dietary supplement. The reference to "acetone-free" means that the product was not subjected to acetone treatment during processing.

DETAILED DESCRIPTION OF THE INVENTION

According to one embodiment, the present invention provides an acetone-free Bowman-Birk inhibitor product having: (i) greater than 65 wt. % soy protein of total dry matter and (ii) a chymotrypsin inhibitor (CI) level of at least 110 milligrams/gram.

According to another embodiment, the present invention provides a method for manufacturing a protein product which method involves: (a) providing a substantially defatted soybean material; (b) removing fiber from said material; and (c) achieving a desired CI content by ultrafiltration. The resulting product which can optionally be dried is then used in a pharmaceutical composition or dietary supplement.

The method of the present invention generally involves: 1) dehulling whole soybeans; 2) flaking the dehulled soybeans; 3) extracting soybean oil from the flaked soybeans with hexane, or a similar solvent; 4) desolventizing the defatted soybean flakes without high heating or toasting to produce "white" flakes; 5) grinding the white flakes to produce soy flour; 6) removing fiber from the soy flour; 7) removing stachyose and raffnose by ultrafiltration, while retaining BBI; and 8) optionally spray drying the resulting concentrate.

Steps 1 through 4 described above are commonly referred to collectively as an extraction process for soybeans. The general procedure for the above-described steps 1 through 4 is well known as exemplified by U.S. Pat. Nos. 5,097,017 to Konwinski and 3,897,574 to Pass and by Serrato, "Extraction of Oil from Soybeans," J. Am. Oil Chem. Soc., 58, 157 (1981) and Becker, "Solvent Extraction of Soybeans," J. Am. Oil Chem. Soc., 55, 754 (1978).

The first step described above involves dehulling soybeans. Dehulling is the process in which the soybean hulls are removed from the whole soybeans. The soybeans are carefully cleaned prior to dehulling to remove foreign matter, so that product will not be contaminated by color bodies. Soybeans also are normally cracked into about 6 to 8 pieces prior to dehulling.

The hull typically accounts for about 8% of the weight of the whole soybean. The dehulled soybean is about 10 wt. % water, 40 wt. % protein, 20 wt. % fat, with the remainder mainly being carbohydrates, fiber and minerals.

The second step described above involves a flaking process. Soybeans are conditioned prior to flaking by adjusting moisture and temperature to make the soybean pieces sufficiently plastic. The conditioned soybean pieces are passed through flaking rolls to form flakes that are about 0.25 to 0.30 mm (0.01 to 0.012 in) thick.

The third step described above involves removing soybean oil from the flakes. The soybean flakes are "defatted" by contacting them with hexane to remove soybean oil. Soybean oil is used in margarine, shortening and other food products, and is a good source of lecithin, which has many useful applications as an emulsifier.

In the fourth step described above, the hexane-defatted soybean flakes are desolventized—hexane is removed—without toasting to produce white flakes. This is different than conventional soybean oil hexane processes where the flakes are toasted and used for animal feed.

In the fifth step described above, the white flakes are ground to make soy flour. In an alternative embodiment, the white flakes can be used without grinding them into soy flour. White flakes tend to cause lower yields, in the range of about 1-2%, because of higher losses tend to occur in the fiber removal operation described below. However, the carryover of fiber in the liquor fraction is significantly reduced when flakes are used.

Soy flour that can be used as a starting material for the subject invention is readily, commercially available. Commercial soy flour typically would have at least 50 wt. % (52.5 wt. %) protein (N×6.25); about 30-40 wt. % (34.6 wt. %) carbohydrates; about 5-10 wt. % (6 wt. %) moisture; about 5-10 wt. % (6 wt. %) ash; about 2-3 wt. % (2.5 wt. %) crude fiber and less than about 1 wt. % (0.9 wt. %) fat (ether extract).

According to one embodiment of the present invention, a soy flour having a protein dispersibility index (PDI) of 90% and a 80 mesh particle size was used. PDI is determined by American Oil Chemists' Society (AOCS) method Ba 10-65. A 90% PDI would indicate soy flour with no heat treatment that is enzyme active. 80 mesh particle size means that greater than 95% of the soy flour passes through a number 80 mesh USA standard sieve.

In the sixth step, the soy flour is slurried with water. According to one embodiment, the slurry has a solids content of about 5-15 wt %. However, a slurry having even lower solids content could be employed according to the present invention.

According to one embodiment of the present invention, the water used to slurry the soy flour is pre-heated to a temperature of about 94° C.

It also usually is necessary to provide some agitation or mixing to slurry the soy flour. One means for providing necessary agitation or mixing is with the use of a propeller-type agitator.

After the soy flour is slurried, fiber can be removed by adjusting the pH of the slurry to about 7-7.5 with sodium hydroxide and separating the slurry to into a cake and liquor. In an alternative embodiment potassium hydroxide could be used to adjust the pH of the slurry and produce a low sodium product if desired.

The separation can be performed by a number of physical separation means; however, centrifugation is an acceptable means that is both efficient and effective. According to one embodiment of the present invention, a scroll-type centrifuge can be used to perform the desired separation. In yet another embodiment of the invention, the separation can be performed using a disc-type or tubular centrifuge.

In the seventh step, the fiber removed liquor is subjected to ultrafiltration to remove oligosaccharides, other sugars and small molecular weight components to make the product that has at least about 80 wt. % protein. During the ultrafiltration process, BBI is retained as indicated by measured CI.

Any spiral bound membrane with a molecular weight cut-off (MWCO) from 1,000 to 200,000 is suitable for used in the ultrafiltration step. A membrane having a MWCO of 10,000 was found to be particularly suitable for purposes of the present invention. Typically, about 75% of the feed volume is removed as permeate during the ultrafiltration.

The ultrafiltered product is pasteurized before being optionally dried. Pasteurization can be accomplished by jet cooking. Alternatively, pasteurization can be accomplished by holding the slurry in a steam jacketed kettle at an elevated temperature. The pasteurization is performed so that the product also tests negative for salmonella and has an acceptable microbial profile.

The fiber removed, ultrafiltered material (the retentate) can be dried to form the high protein content BBI concentrate. Drying can be accomplished using a vertical spray dryer with a high-pressure nozzle, or any other suitable drying apparatus.

The method used for chymotrypsin inhibitor (CI) analysis is based on the American Oil Chemists' Society (AOCS) official method Ba-12-75 for trypsin inhibitor activity for soy products, differing in the enzyme and substrate used. The substrate used for CI analysis is N-Glutaryl-LPhenylaianine-p-nitroanilide (GPNA), available from Sigma Chemicals as 62505. The enzyme used is L-Chymotrypsin, Type II-Bovine pancreatic alpha chymotrypsin, available from Sigma Chemicals as C4129. The AOCS method is based upon Kakade et al. (Cereal Chemistry, 51. 376 (1974)).

Chymotrypsin hydrolyzes the substrate glutaryl-L-phenylalanine-p-nitroanilide present in excess. The release of p-nitroanilide, a yellow dye, is measured spectrophotometrically. In the presence of soy protein product, the release of p-nitroanilide changes inversely with the level of active chymotrypsin inhibitor.

These and other aspects of the present invention may be more readily understood by reference to one or more of the following examples. In the examples and throughout percentages are by weight unless otherwise indicated. All results are on dry-basis unless otherwise indicated.

EXAMPLE 1

About 22.5 kilograms (50 pounds) of soy flour having a protein dispersibility index (PDI) of 86% was dispersed in about 245 liters (65 gallons) of water at about 60° C. and the pH was adjusted to about 7.5 using sodium hydroxide. The suspension was mixed for 30 minutes at about 60° C., and then centrifuged in a decanting centrifuge. The insoluble centrifuge cake was discarded, and the supernatant was heat treated by passing it through a jet cooker at about 121° C. with a holding time of 15 seconds. The suspension was then cooled to about 38° C. in a jacketed vessel. The cooled suspension was ultrafiltered using a 10,000 molecular weight cutoff (MWCO) spiral wound membrane to remove about 75% of the feed volume as permeate. The retentate from the membrane was heat treated by passing it through a jet cooker at about 93° C. with a holding time of 15 seconds. The retentate was then cooled to 60° C. in a jacketed vessel and spray dried. This same procedure was repeated a second time to verify the results which are listed in TABLE 1 below.

TABLE 1

|  | Run 1 | Run 2 |
|---|---|---|
| Protein (dry basis) (%) | 79.79 | 82.97 |
| Total Isoflavones (dry basis)(mg/g) | 2.18 | 3.51 |
| Moisture (%) | 1.23 | 3.73 |
| Ash (as is) (%) | 6.87 | 6.50 |
| Crude Fiber (as is)(%) | 0.80 | 0.80 |
| Nitrogen Solubility Index (NSI)(%) | 96.99 | 95.45 |
| CI Content (mg/g) | 178 | >160 |

In conjunction with this Example, the same procedure was again repeated and the resulting product was analyzed for lunasin content. It was found that the product contained 19 wt. % lunasin, indicating the BBI product of the present invention is a viable source of lunasin which is effective in inhibiting the malignant transformation of cells.

EXAMPLE 2

About 227 liters (60 gallons) of water were added to a mixing tank and heated to 60° C. Then, about 45 kilograms (100 pounds) of soy flakes were added to the mixing tank to form a slurry. The pH of the slurry was adjusted to about 7.1, using about 1400 ml of 4.5% NaOH solution. The slurry was mixed for 10 minutes at a temperature of about 55° C. to about 58° C. and then transferred to a centrifuge feed tank, which contained about 303 liters (80 gallons) of water preheated to a temperature of about 60° C. The diluted slurry was mixed for about 20 minutes at a temperature of about 55° C. to about 58° C. and thereafter fed at a rate of about 7.6 liters (2 gallons) per minute to a Sharples scroll-type centrifuge. The supernatant (suspension) was jet cooked at a temperature of about 127° C. The jet-cooked suspension was transferred to a membrane feed tank through a 100-mesh strainer. About 10 grams of sodium metabisulfite was added to the membrane feed tank. The suspension was fed to an ultrafiltration membrane system containing a spiral-wound membrane with a MWCO of 10,000. The temperature of the suspension was maintained at about 26.5°-26.8° C. during membrane processing. About 75% of the original feed volume added to the membrane feed tank was removed as permeate. The retentate from the membrane system was pasteurized at about 76.7° C. and spray dried using a high-pressure pump feeding a spray nozzle in a vertical spray dryer. The dried product was analyzed to determine the content thereof. The results of the analysis are shown in TABLE 2 below.

TABLE 2

| Composition | wt. % | mg/g of total dry matter |
|---|---|---|
| protein | 82.73 |  |
| crude fiber | 0.94 |  |
| crude fat | 0.01 |  |
| ash | 5.91 |  |
| fructose |  | 2.90 |
| galactose |  | 1.33 |
| sucrose |  | 40.29 |
| raffinose |  | 6.88 |
| stachyose |  | 30.13 |
| isoflavones |  | 4.54 |
| Daidzin |  | 0.77 |
| Glycitin |  | 0.22 |
| Genistin |  | 1.00 |
| 6"-O-malonyldaidzin |  | 0.91 |
| 6"-O-malonylglycitin |  | 0.16 |
| 6"-O-acetyl genistin |  | 0.12 |
| 6"-O-malonylgenistin |  | 1.24 |
| Daidzein |  | 0.05 |
| Genistein |  | 0.07 |
| Soyasapogenols |  | 4.06 |
| soyasapogenol A |  | 1.25 |
| soyasapogenol B |  | 2.81 |
| nitrogen solubility index (NSI)(%) | 92 |  |
| chymotrypsin inhibitor (CI) |  | 164.7 |

EXAMPLE 3

About 227 liters (60 gallons) of water were added to a mixing tank and heated to a temperature of about 60° C. Then, about 45 kilograms (100 pounds) of soy white flakes were added to the mixing tank to form a slurry. The pH of the slurry was adjusted to about 7.08, using about 1400 ml of 4.5% NaOH solution. The slurry was mixed for 10 minutes at a temperature of about 55° C. to about 58° C. and then transferred to a centrifuge feed tank, which contained about 303 liters (80 gallons) of water preheated to a temperature of about 60° C. The diluted slurry was mixed for about 20 minutes at a temperature of about 55° C. to about 58° C. and thereafter fed at a rate of about 7.6 liters (2 gallons) per minute to a Sharples scroll-type centrifuge. The supernatant (suspension) was jet cooked at a temperature of about 127° C. The jet-cooked suspension was transferred to a membrane feed tank through a 100-mesh strainer. The suspension was fed to an ultrafiltration membrane system containing a spiral-wound membrane with a MWCO of 10,000. The temperature of the suspension was maintained at about 48.8° C. to about 49° C. during membrane processing. About 75% of the original feed volume added to the membrane feed tank was removed as permeate. The retentate from the membrane system was pasteurized at a temperature of about 76.7° C. and spray dried using a high-pressure pump feeding a spray nozzle in a vertical spray dryer. The dried product was analyzed to determine the content thereof. The results of the analysis are shown in TABLE 3 below.

TABLE 3

| Composition | wt. % | mg/g of total dry matter |
|---|---|---|
| protein | 82.81 |  |
| crude fiber | 0.84 |  |
| crude fat | 0.13 |  |
| ash | 6.00 |  |
| fructose |  | 2.72 |
| galactose |  | 1.21 |

TABLE 3-continued

| Composition | wt. % | mg/g of total dry matter |
|---|---|---|
| sucrose | | 30.11 |
| raffinose | | 4.99 |
| stachyose | | 21.80 |
| isoflavones | | 3.54 |
| Daidzin | | 0.67 |
| Glycitin | | 0.09 |
| Genistin | | 0.90 |
| 6"-O-malonyldaidzin | | 0.61 |
| 6"-O-malonylglycitin | | 0.08 |
| 6"-O-acetyl genistin | | 0.16 |
| 6"-O-malonylgenistin | | 0.96 |
| Daidzein | | 0.03 |
| Genistein | | 0.04 |
| Soyasapogenols | | 3.98 |
| soyasapogenol A | | 1.05 |
| soyasapogenol B | | 2.93 |
| nitrogen solubility index (NSI)(%) | 93.8 | |
| chymotrypsin inhibitor (CI) | | 173.3 |

EXAMPLE 4

About 227 liters (60 gallons) of water were added to a mixing tank and heated to a temperature of about 60° C. Then, about 45 kilograms (100 pounds) of soy flour were added to the mixing tank to form a slurry. The pH of the slurry was adjusted to about 7.08, using about 1400 ml of 4.5% NaOH solution. The slurry was mixed for 10 minutes at a temperature of about 55° C. to about 58° C. and then transferred to a centrifuge feed tank, which contained about 303 liters (80 gallons) of water preheated to a temperature of about 60° C. The diluted slurry was mixed for about 20 minutes at a temperature of about 55° C. to about 58° C. and thereafter fed at a rate of about 7.6 liters (2 gallons) per minute to a Sharples scroll-type centrifuge. The supernatant (suspension) was jet cooked at a temperature of about 127° C. The jet-cooked suspension was transferred to a membrane feed tank through a 100-mesh strainer. The suspension was fed to an ultrafiltration membrane system containing a spiral-wound membrane with a MWCO of 30,000. The temperature of the suspension was maintained at about 48.8° C. to about 49° C. during membrane processing. About 75% of the original feed volume added to the membrane feed tank was removed as permeate. The retentate from the membrane system was pasteurized at a temperature of about 76.7° C. and spray dried using a high-pressure pump feeding a spray nozzle in a vertical spray dryer. The dried product was analyzed to determine the content thereof. The results of the analysis are shown in TABLE 4 below.

TABLE 4

| Composition | wt. % | mg/g Of total dry matter |
|---|---|---|
| protein | 82.31 | |
| crude fiber | 1.14 | |
| crude fat | 0.01 | |
| ash | 5.44 | |
| fructose | | 2.79 |
| galactose | | 1.60 |
| sucrose | | 33.14 |
| raffinose | | 5.88 |
| stachyose | | 24.24 |
| isoflavones | | 3.53 |
| Daidzin | | 0.60 |
| Glycitin | | 0.17 |

TABLE 4-continued

| Composition | wt. % | mg/g Of total dry matter |
|---|---|---|
| genistin | | 0.70 |
| 6"-O-malonyldaidzin | | 0.76 |
| 6"-O-malonylglycitin | | 0.11 |
| 6"-O-acetyl genistin | | 0.09 |
| 6"-O-malonylgenistin | | 0.99 |
| daidzein | | 0.04 |
| genistein | | 0.07 |
| soyasapogenols | | 3.74 |
| Soyasapogenol A | | 1.04 |
| Soyasapogenol B | | 2.70 |
| nitrogen solubility index (NSI)(%) | 89.2 | |
| chymotrypsin inhibitor (CI) | | 163.3 |

EXAMPLE 5

About 227 liters (60 gallons) of water were added to a mixing tank and heated to a temperature of about 60° C. Then, about 45 kilograms (100 pounds) of soy flour were added to the mixing tank to form a slurry. The pH of the slurry was adjusted to about 7.0, using about 1400 ml of 4.5% NaOH solution. The slurry was mixed for 10 minutes at a temperature of about 55° C. to about 58° C. and then transferred to a centrifuge feed tank, which contained about 303 liters (80 gallons) of water preheated to a temperature of about 60° C. The diluted slurry was mixed for about 20 minutes at a temperature of about 55° C. to about 58° C. and thereafter fed at a rate of about 7.6 liters (2 gallons) per minute to a Sharples scroll-type centrifuge. The supernatant (suspension) was jet cooked at a temperature of about 127° C. The jet-cooked suspension was transferred to a membrane feed tank through a 100-mesh strainer. The suspension was fed to an ultrafiltration membrane system containing a spiral-wound membrane with a MWCO of 1,000,000. The temperature of the suspension was maintained at about 48.8° C. to about 49° C. during membrane processing. About 75% of the original feed volume added to the membrane feed tank was removed as permeate. The retentate from the membrane system was pasteurized at a temperature of about 76.7° C. and spray dried using a high-pressure pump feeding a spray nozzle in a vertical spray dryer. The dried product was analyzed to determine the content thereof. The results of the analysis are shown in TABLE 5 below.

TABLE 5

| Composition | wt. % | mg/g of total dry matter |
|---|---|---|
| protein | 82.32 | |
| crude fiber | 1.25 | |
| crude fat | 0.07 | |
| ash | 5.72 | |
| fructose | | 2.78 |
| galactose | | 1.38 |
| sucrose | | 36.44 |
| raffinose | | 6.82 |
| stachyose | | 26.07 |
| isoflavones | | 3.37 |
| Daidzin | | 0.54 |
| Glycitin | | 0.16 |
| Genistin | | 0.69 |
| 6"-O-malonyldaidzin | | 0.74 |
| 6"-O-malonylglycitin | | 0.11 |
| 6"-O-acetyl genistin | | 0.10 |
| 6"-O-malonylgenistin | | 0.98 |
| Daidzein | | 0.02 |

TABLE 5-continued

| Composition | wt. % | mg/g of total dry matter |
|---|---|---|
| Genistein | | 0.03 |
| Soyasapogenols | | 3.55 |
| soyasapogenol A | | 1.04 |
| soyasapogenol B | | 2.51 |
| nitrogen solubility index (NSI)(%) | 90.7 | |
| chymotrypsin inhibitor (CI) | | 167.5 |

From the results of Examples 1-5 it can be seen that the product produced by the present method, whether using soy flour or soy flakes as a starting material, had a protein content of 79 wt. % or greater and a CI content of greater than 150 mg/g, in addition to a nitrogen solubility index of about 85% or greater and an isoflavones content that is generally greater than about 2.00 mg/g.

It thus can be appreciated that the product produced of the present invention has the desired properties of a high protein soy isolate together with a high BBI content as indicted by the CI values.

Although the present invention has been described with reference to particular means, materials and embodiments, from the foregoing description, one skilled in the art can easily ascertain the essential characteristics of the present invention and various changes and modifications can be made to adapt the various uses and characteristics without departing from the spirit and scope of the present invention as set forth in the following claims.

What is claimed:

1. A Bowman-Birk inhibitor soy protein concentrate product having more than about 65 wt.% soy protein on a dry basis and a chymotrypsin inhibitor level of at least 110 mg/g, wherein the Bowman-Birk inhibitor soy protein concentrate product is derived from a non-acidic aqueous extract of soy flour.

2. The product of claim 1, wherein the product is acetone-free.

3. The product of claim 1, wherein the product was not extracted with alcohol.

4. The product of claim 1, wherein the product has about 70-85 wt.% soy protein on a dry basis.

5. The product of claim 1, wherein the product has a chymotrypsin inhibitor level of greater than about 150 mg/g.

6. A pharmaceutical composition that is made from the product of claim 1.

7. A dietary supplement that is made from the product of claim 1.

* * * * *